(12) United States Patent
Karatzas et al.

(10) Patent No.: US 7,157,615 B2
(45) Date of Patent: *Jan. 2, 2007

(54) PRODUCTION OF BIOFILAMENTS IN TRANSGENIC ANIMALS

(75) Inventors: Costas N. Karatzas, Quebec (CA); Jeffrey D. Turner, Quebec (CA); Anthoula Lazaris-Karatzas, Quebec (CA)

(73) Assignee: Nexia Biotechnologies, Inc., Montreal ( * ) Notice: This patent issued on a continued prosecution application filed under 37 CFR 1.53(d), and is subject to the twenty year patent term provisions of 35 U.S.C. 154 (a)(2).

Subject to any disclaimer, the term of this patent is extended or adjusted under 35 U.S.C. 154(b) by 0 days.

(21) Appl. No.: 09/040,518

(22) Filed: Mar. 17, 1998

(65) Prior Publication Data

US 2001/0042255 A1 Nov. 15, 2001

(51) Int. Cl.
*C12P 21/00* (2006.01)
*A01K 67/00* (2006.01)
*A01K 67/033* (2006.01)
*A01K 67/027* (2006.01)

(52) U.S. Cl. .................. 800/7; 800/4; 800/13; 800/14; 800/15; 800/16

(58) Field of Classification Search .................. 800/4, 800/7, 13, 14, 15, 16, 17, 18; 536/23.5; 435/455, 435/325, 70.1, 70.3, 69.1
See application file for complete search history.

(56) References Cited

U.S. PATENT DOCUMENTS

| 4,423,145 A | 12/1983 | Stampfer et al. |
| 4,873,316 A | 10/1989 | Meade et al. |
| 5,227,301 A | 7/1993 | Turner et al. |
| 5,243,038 A | 9/1993 | Ferrari et al. |
| 5,304,489 A | 4/1994 | Rosen |

FOREIGN PATENT DOCUMENTS

| EP | 0 771 874 A2 | 7/1997 |
| WO | WO88/01648 | 3/1988 |
| WO | WO91/08216 | 6/1991 |
| WO | WO93/25567 | 12/1993 |
| WO | WO96/39494 | 12/1996 |
| WO | WO 97/08315 | 6/1997 |

OTHER PUBLICATIONS

Bradley et al. Modifying the mouse: Design and desire. Bio/Technology 10: 534-539, May 1992.*
Campbell and Wilmut, Totipotency and multipotentiality of cultured cells: Applications and progress. Theriogenology 47: 63-72, Jan. 1997.*
Wall, R.J. Transgenic livestock: Progress and prospects for the future. Theriogenology 45: 57-68, May 1992.*
Hayashi et al., "Evidence from Flagelliform Silk cDNA for the Structural Basis of Elasticity and Modular Nature of Spider Silks," Journal of Molecular Biology 275:773-784 (1998).
Kerr et al., "The Bladder as a Bioreactor: Urothelium Production and Secretion of Growth Hormone into Urine," Nature Biotechnology 16:75-79 (1998).
Meyer-Puttlitz et al., "Ectopic Expression of a Bacterial *lacZ* Gene in the Limbic System of Transgenic Mice," NeuroReport 6:1674-1678 (1995).
Lee et al., "Production of Biomedical Proteins in the Milk of Transgenic Dairy Cows: the State of the Art," Journal of Controlled Release 29:213-221 (1994).
Parkhe et al., "Structural Studies of Spider Silk Proteins in the Fiber," Journal of Molecular Recognition 10:1-6 (1997).
Prince et al., "Construction, Cloning, and Expression of Synthetic Genes Encoding Spider Dragline Silk," Biochemistry 34:10879-10885 (1995).
Romagnolo et al., "Transgenic Approaches for Modifying the Mammary Gland to Produce Therapeutic Proteins," Environmental Health Perspectives 102:846-851 (1994).
Guerette et al., "Silk Properties Determined by Gland-Specific Expression of a Spider Fibroin Gene Family," Science 272: 112-115, 1996.
Arcidiacono et al., "Purification and characterization of Recombinant Spider Expressed in *Escherichia coli*," Appl. Microbiol. Biotechnol. 49: 31-38, 1998.
Gosline et al., "The Macromolecular Design of Spiders' Silks," Biomimetics: Design and Processing of Materials, pp. 237-261, eds. Sarikaya and Aksay, Amer. Inst. of Physics, 1995.
Xu and Lewis, "Structure of a Protein Superfiber: Spider Dragline silk," Proc. Natl. Acad. Sci. U.S.A. 87: 7120-7124, 1990.
Beckwitt and Arcidiacono, "Sequence Conservation in the C-Terminal Region of Spider Silk Protein (Spidroin) from *Nephila clavipes* (Tetragnathidae) and *Araneus bicentenarius* (Araneidae)," J. Biol. Chem. 269: 6661-6663, 1994.
Fahnestock and Irwin, "Synthetic Spider Dragline Silk Proteins and their Production in *Escherichia coli*," Appl. Microbiol. Biotechnol. 47: 23-32, 1997.

(Continued)

*Primary Examiner*—Anne-Marie Falk
(74) *Attorney, Agent, or Firm*—Jones Day

(57) ABSTRACT

Disclosed is a method for the recombinant production of biofilaments, such as spider silk or insect fibroins, using transgenic animals which secrete the biofilaments in their milk and/or urine, and transgenic cells which secrete the biofilaments into culture media. Such a method is useful for producing large quantities of biofilament material. Also disclosed is a nucleic acid molecule for generating such transgenic animals.

6 Claims, 2 Drawing Sheets

OTHER PUBLICATIONS

Lee et al., "Tissue-Specific Expression of the rat β -Casein Gene in Transgenic Mice," Nucleic Acids Res. 16: 1027-1041, 1988.

Vilotte et al., "Efficient Tissue-Specific Expression of Bovine α-Lactalbumin in Transgenic Mice," Eur. J. Biochem. 186: 43-48, 1989.

Tsujimoto and Suzuki, "The DNA Sequence of Bombyx mori Fibroin Gene Including the 5' Flanking, mRNA Coding, Entire Intervening and Fibroin Protein Coding Regions," Cell 18: 591-600, 1979.

Tsujimoto and Suzuki, "Structural Analysis of the Fibroin Gene at the 5' End and its Surrounding Regions," Cell 16: 425-436, 1979.

Huynh et al., "Establishment of Bovine Mammary Epithelial Cells (MAC-T): An in Vitro Model for Bovine Lactation," Exp. Cell. Res. 197: 191-199, 1991.

Ichimura and Mita, "Essential Role of Duplications of Short Motif Sequences in the Genomic Evolution to *Bombyx mori*," J. Mol. Evol. 35: 123-130, 1992.

Ebert et al., "Induction of Human Tissue Plasminogen Activator in the Mammary Gland of Transgenic Goats," Bio/Technology 12: 699-701, 1994.

Velander et al., "High-level Expression of a Heterologous Protein in the Milk of Transgenic Swine Using the cDNA Encoding Human Protein C," Proc. Natl. Acad. Sci. U.S.A. 89: 12003-12007, 1992.

Velander et al., "Production of Biologically Active Human Protein C in the Milk of Transgenic Mice," Ann. N. Y. Acad Sci. 665: 391-403, 1992.

Campbell et al., "Comparison of the Whey Acidic Protein Genes of the Rat and Mouse," Nucleic Acids Res. 12: 8685-8697, 1984.

Hennighausen et al., "Comprarative Sequence Analysis of the mRNAs Coding for Mouse and Rat Whey Protein," Nucl. Acids Res. 10: 3733-3744, 1982.

Lin et al., "A Tissue-Specific Promoter that Can Drive a Foreign Gene to Express in the Suprabasal Urothelial Cells of Transgenic Mice" Proc. Natl. Acad. Sci. U.S.A. 92:679-683, 1995.

Peschon et al., "Supermatid-Specific Expression of Protamine 1 in Transgenic Mice," Proc. Natl. Acad. Sci. U.S.A. 84: 5316-5319, 1987.

Groenen and Van der Poel, "Regulation of Expression of Milk Protein Genes: A Review," Livestock Production Science 38: 61-78, 1994.

* cited by examiner

Figure 1A beta casein/ NcDS-1
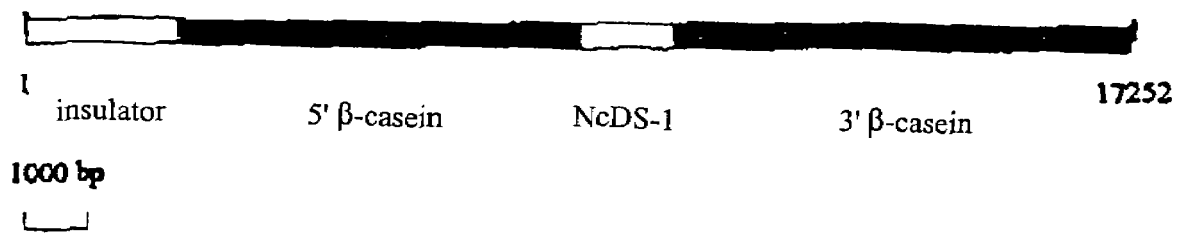

Figure 1B  WAP/NcDS-1 construct
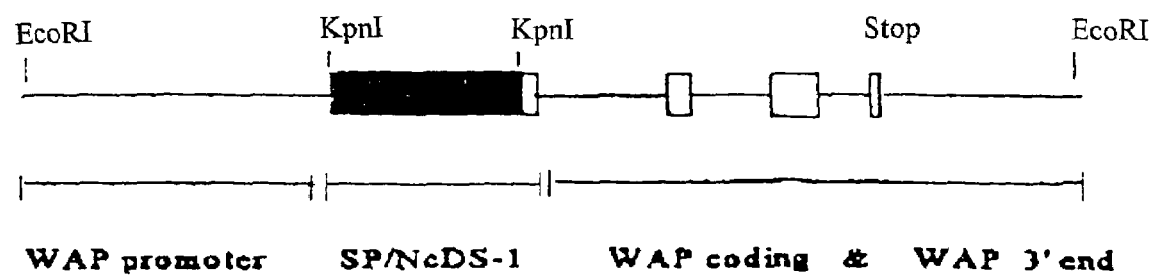
WAP promoter   SP/NcDS-1   WAP coding & WAP 3' end
Figure 1C  Uroplakin II/ NcDS-1 construct
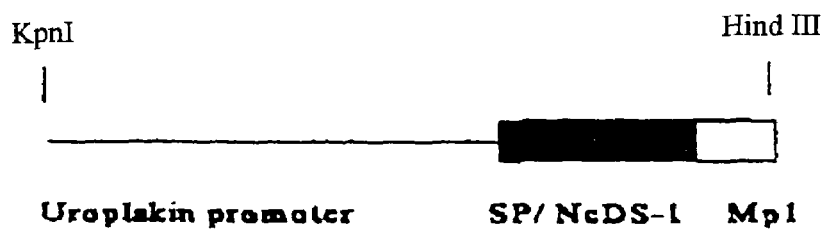
Uroplakin promoter   SP/NcDS-1   Mp1

SEQUENCE LISTING

<160> NUMBER OF SEQ ID NOS: 32

<210> SEQ ID NO 1
<211> LENGTH: 6
<212> TYPE: PRT
<213> ORGANISM: Bombyx mori

<400> SEQUENCE: 1

```
Gly Ala Gly Ala Gly Ser
  1               5
```

<210> SEQ ID NO 2
<211> LENGTH: 34
<212> TYPE: PRT
<213> ORGANISM: Nephila clavipes

<400> SEQUENCE: 2

```
Ala Gly Gln Gly Gly Tyr Gly Gly Leu Gly Ser Gln Gly Ala Gly Arg
  1               5                  10                  15
Gly Gly Leu Gly Gly Gln Gly Ala Gly Ala Ala Ala Ala Ala Ala
             20                  25                  30
Gly Gly
```

<210> SEQ ID NO 3
<211> LENGTH: 47
<212> TYPE: PRT
<213> ORGANISM: Nephila clavipes

<400> SEQUENCE: 3

```
Cys Pro Gly Gly Tyr Gly Pro Gly Gln Gln Cys Pro Gly Gly Tyr Gly
  1               5                  10                  15
Pro Gly Gln Gln Cys Pro Gly Gly Tyr Gly Pro Gly Gln Gln Gly Pro
             20                  25                  30
Ser Gly Pro Gly Ser Ala Ala Ala Ala Ala Ala Ala Ala
             35                  40                  45
```

<210> SEQ ID NO 4
<211> LENGTH: 8
<212> TYPE: PRT
<213> ORGANISM: Nephila clavipes

<400> SEQUENCE: 4

```
Gly Gly Ala Gly Gln Gly Gly Tyr
  1               5
```

<210> SEQ ID NO 5
<211> LENGTH: 4
<212> TYPE: PRT
<213> ORGANISM: Artificial Sequence
<220> FEATURE:
<223> OTHER INFORMATION: Designed peptide to act as a recognition site
      for an enzyme

<400> SEQUENCE: 5

```
Asp Asp Asp Lys
  1
```

<210> SEQ ID NO 6
<211> LENGTH: 4
<212> TYPE: PRT
<213> ORGANISM: Artificial Sequence
<220> FEATURE:
<223> OTHER INFORMATION: Designed to act as a recognition site for an
      enzyme

<400> SEQUENCE: 6

```
Ile Glu Gly Arg
  1
```

<210> SEQ ID NO 7
<211> LENGTH: 8

```
<212> TYPE: PRT
<213> ORGANISM: Artificial Sequence
<220> FEATURE:
<223> OTHER INFORMATION: Designed peptide to act as a recognition site
      for an enzyme

<400> SEQUENCE: 7

Tyr Ile His Pro Phe His Leu Leu
1               5

<210> SEQ ID NO 8
<211> LENGTH: 4
<212> TYPE: PRT
<213> ORGANISM: Artificial Sequence
<220> FEATURE:
<223> OTHER INFORMATION: Designed peptide to act as a recognition site
      for an enzyme

<400> SEQUENCE: 8

Arg Gly Pro Arg
1

<210> SEQ ID NO 9
<211> LENGTH: 5
<212> TYPE: PRT
<213> ORGANISM: Nephila clavipes

<400> SEQUENCE: 9

Ala Ala Ala Ala Ala
1               5

<210> SEQ ID NO 10
<211> LENGTH: 4
<212> TYPE: PRT
<213> ORGANISM: Nephila clavipes

<400> SEQUENCE: 10

Gly Ala Gly Ala
1

<210> SEQ ID NO 11
<211> LENGTH: 6
<212> TYPE: PRT
<213> ORGANISM: Nephila clavipes

<400> SEQUENCE: 11

Gly Ala Gly Ala Gly Ala
1               5

<210> SEQ ID NO 12
<211> LENGTH: 8
<212> TYPE: PRT
<213> ORGANISM: Nephila clavipes

<400> SEQUENCE: 12

Gly Ala Gly Ala Gly Ala Gly Ala
1               5

<210> SEQ ID NO 13
<211> LENGTH: 10
<212> TYPE: PRT
<213> ORGANISM: Nephila clavipes

<400> SEQUENCE: 13

Gly Ala Gly Ala Gly Ala Gly Ala Gly Ala
1               5                   10
```

```
<210> SEQ ID NO 14
<211> LENGTH: 12
<212> TYPE: PRT
<213> ORGANISM: Nephila clavipes

<400> SEQUENCE: 14

Gly Ala Gly Ala Gly Ala Gly Ala Gly Ala Gly Ala
 1               5                  10

<210> SEQ ID NO 15
<211> LENGTH: 14
<212> TYPE: PRT
<213> ORGANISM: Nephila clavipes

<400> SEQUENCE: 15

Gly Ala Gly Ala Gly Ala Gly Ala Gly Ala Gly Ala Gly Ala
 1               5                  10

<210> SEQ ID NO 16
<211> LENGTH: 7
<212> TYPE: PRT
<213> ORGANISM: Nephila clavipes

<400> SEQUENCE: 16

Gly Gly Tyr Gly Gln Gly Tyr
 1               5

<210> SEQ ID NO 17
<211> LENGTH: 8
<212> TYPE: PRT
<213> ORGANISM: Nephila clavipes

<400> SEQUENCE: 17

Ala Ala Ala Ala Ala Ala Ala Ala
 1               5

<210> SEQ ID NO 18
<211> LENGTH: 8
<212> TYPE: PRT
<213> ORGANISM: Nephila clavipes

<400> SEQUENCE: 18

Gly Gly Ala Gly Gln Gly Gly Tyr
 1               5

<210> SEQ ID NO 19
<211> LENGTH: 17
<212> TYPE: PRT
<213> ORGANISM: Nephila clavipes

<400> SEQUENCE: 19

Gly Gly Gln Gly Gly Gln Gly Gly Tyr Gly Gly Leu Gly Ser Gln Gly
 1               5                  10                  15

Ala

<210> SEQ ID NO 20
<211> LENGTH: 8
<212> TYPE: PRT
<213> ORGANISM: Nephila clavipes

<400> SEQUENCE: 20

Ala Ser Ala Ala Ala Ala Ala Ala
 1               5
```

<210> SEQ ID NO 21
<211> LENGTH: 5
<212> TYPE: PRT
<213> ORGANISM: Nephila clavipes

<400> SEQUENCE: 21

Gly Pro Gly Gln Gln
 1               5

<210> SEQ ID NO 22
<211> LENGTH: 10
<212> TYPE: PRT
<213> ORGANISM: Nephila clavipes

<400> SEQUENCE: 22

Gly Pro Gly Gln Gln Gly Pro Gly Gln Gln
 1               5                  10

<210> SEQ ID NO 23
<211> LENGTH: 15
<212> TYPE: PRT
<213> ORGANISM: Nephila clavipes

<400> SEQUENCE: 23

Gly Pro Gly Gln Gln Gly Pro Gly Gln Gln Gly Pro Gly Gln Gln
 1               5                  10                  15

<210> SEQ ID NO 24
<211> LENGTH: 20
<212> TYPE: PRT
<213> ORGANISM: Nephila clavipes

<400> SEQUENCE: 24

Gly Pro Gly Gln Gln Gly Pro Gly Gln Gln Gly Pro Gly Gln Gln Gly
 1               5                  10                  15

Pro Gly Gln Gln
            20

<210> SEQ ID NO 25
<211> LENGTH: 25
<212> TYPE: PRT
<213> ORGANISM: Nephila clavipes

<400> SEQUENCE: 25

Gly Pro Gly Gln Gln Gly Pro Gly Gln Gln Gly Pro Gly Gln Gln Gly
 1               5                  10                  15

Pro Gly Gln Gln Gly Pro Gly Gln Gln
            20                  25

<210> SEQ ID NO 26
<211> LENGTH: 30
<212> TYPE: PRT
<213> ORGANISM: Nephila clavipes

<400> SEQUENCE: 26

Gly Pro Gly Gln Gln Gly Pro Gly Gln Gln Gly Pro Gly Gln Gln Gly
 1               5                  10                  15

Pro Gly Gln Gln Gly Pro Gly Gln Gln Gly Pro Gly Gln Gln
            20                  25                  30

<210> SEQ ID NO 27
<211> LENGTH: 35

```
<212> TYPE: PRT
<213> ORGANISM: Nephila clavipes

<400> SEQUENCE: 27

Gly Pro Gly Gln Gln Gly Pro Gly Gln Gln Gly Pro Gly Gln Gln Gly
1               5                   10                  15
Pro Gly Gln Gln Gly Pro Gly Gln Gln Gly Pro Gly Gln Gln Gly Pro
            20                  25                  30
Gly Gln Gln
        35

<210> SEQ ID NO 28
<211> LENGTH: 40
<212> TYPE: PRT
<213> ORGANISM: Nephila clavipes

<400> SEQUENCE: 28

Gly Pro Gly Gln Gln Gly Pro Gly Gln Gln Gly Pro Gly Gln Gln Gly
1               5                   10                  15
Pro Gly Gln Gln Gly Pro Gly Gln Gln Gly Pro Gly Gln Gln Gly Pro
            20                  25                  30
Gly Gln Gln Gly Pro Gly Gln Gln
        35                  40

<210> SEQ ID NO 29
<211> LENGTH: 11
<212> TYPE: PRT
<213> ORGANISM: Nephila clavipes

<400> SEQUENCE: 29

Gly Pro Gly Gly Gln Gly Pro Tyr Gly Pro Gly
1               5                   10

<210> SEQ ID NO 30
<211> LENGTH: 10
<212> TYPE: PRT
<213> ORGANISM: Nephila clavipes

<400> SEQUENCE: 30

Ser Ser Ala Ala Ala Ala Ala Ala Ala Ala
1               5                   10

<210> SEQ ID NO 31
<211> LENGTH: 8
<212> TYPE: PRT
<213> ORGANISM: Nephila clavipes

<400> SEQUENCE: 31

Gly Pro Gly Ser Gln Gly Pro Ser
1               5

<210> SEQ ID NO 32
<211> LENGTH: 5
<212> TYPE: PRT
<213> ORGANISM: Nephila clavipes

<400> SEQUENCE: 32

Gly Pro Gly Gly Tyr
1               5
```

PRODUCTION OF BIOFILAMENTS IN TRANSGENIC ANIMALS

BACKGROUND OF THE INVENTION

The utility of spider silk proteins as "super filaments" has led to attempts to produce recombinant spider dragline silks (Prince et al., Biochemistry 34: 10879 –10885, 1995; Fahnestock and Irwin, Appl. Microbiol. Biotechnol. 47: 23 –32, 1997; Fahnestock and Bedzyk, Appl. Microbiol. Biotechnol. 47: 33 –39, 1997). Although successful expression of spider's silk has been demonstrated in *E. coli*, significant problems remain, such as instability of the sequences used due to recombination and rearrangement in the repetitive areas of the gene, inefficient transcription, translational pausing and premature termination of synthesis resulting in limitations on the length of the silk that can be produced efficiently (less than or equal to 1000 amino acids), low protein yields (4 to 300 mg/liter), and low solubility of the produced fiber.

Production of synthetic spider dragline silk protein in the methylotropic yeast *Pichia Pastoris* was superior to that of *E. coli* in that longer proteins of at least 1600 amino acids in length could be produced efficiently with no observed size heterogeneity due to premature termination of synthesis and stability of the repetitive sequences in the genes being expressed. Yields of protein in the *Pichia* system were 663 mg/liter; however, only 15% of this was in a soluble form in the yeast cell lysate.

SUMMARY OF THE INVENTION

We have discovered a method for producing biofilaments (e.g., spider silk protein) in transgenic animals. This method greatly facilitates the production of these proteins, which are useful as "super filaments."

In a first aspect, the invention features a nucleic acid molecule that includes (i) a nucleic acid sequence encoding a biofilament, (ii) a promoter that directs expression of a polypeptide in milk-producing cells or urine-producing cells, where the promoter is operably linked to the nucleic acid sequence, and (iii) a leader sequence that enables secretion of the biofilament by the milk-producing cells or the urine-producing cells, into the milk or urine of a mammal, respectively.

In a second aspect, the invention features a mammalian embryo whose nucleus contains a nucleic acid molecule that includes (i) a nucleic acid sequence encoding a biofilament, (ii) a promoter that directs expression of a polypeptide in milk-producing cells or urine-producing cells, where the promoter is operably linked to the nucleic acid sequence, and (iii) a leader sequence that enables secretion of the biofilament by the milk-producing cells or the urine-producing cells, into, respectively, milk or urine of the mammal that develops from the nucleic acid molecule-containing embryo. Preferably, the nucleic acid molecule is inserted by artifice.

In a third aspect, the invention features a female mammal in which the genome of the mammary tissue of the female mammal contains a nucleic acid molecule that includes (i) a nucleic acid sequence encoding a biofilament, (ii) a promoter that directs expression of a polypeptide in milk-producing cells, where the promoter is operably linked to the nucleic acid sequence, and (iii) a leader sequence that enables secretion of the biofilament by the milk-producing cells, into milk of the female mammal. Preferably, the female mammal is a rodent, a ruminant, or a goat.

In a fourth aspect, the invention features an animal in which the genome of cells that contribute to urine production in the animal contains a nucleic acid molecule that includes (i) a nucleic acid sequence encoding a biofilament, (ii) a promoter that directs expression of a polypeptide urine-producing cells, where the promoter is operably linked to the nucleic acid sequence, and (iii) a leader sequence that enables secretion of the biofilament by the urine-producing cells, into urine of the animal. Preferably, the animal is a mammal.

In one embodiment of all of the above aspects of the invention, the biofilament is spider silk (e.g., dragline silk). In another embodiment of all of the above aspects, the nucleic acid molecule includes an intron. In a preferred embodiment, when secreted such that the secretion is subjected to shear forces and mechanical extension, the biofilament has a poly-alanine segment that undergoes a helix to a β-sheet transition, where the transition forms a β-crystal that stabilizes the structure of the biofilament.

In another preferred embodiment of all of the above aspects of the invention, the biofilament has an amorphous domain that forms a β-pleated sheet such that inter-β sheet spacings are between 3 angstroms and 8 angstroms in size. In yet another preferred embodiment, the biofilament has a C-terminal amino acid motif containing an amorphous domain and a crystal forming domain, where the motif has a sequence that is at least 50% identical to SEQ ID NO:2. In yet another preferred embodiment, the biofilament has a consensus sequence that is at least 50% identical to SEQ ID NO:3. In In a fifth aspect, the invention features a method for producing a biofilament that includes the steps of: (a) providing an embryonal cell transfected with a biofilament-encoding nucleic acid molecule that expresses and causes secretion of the biofilament from a cell derived from the transfected embryonal cell; (b) growing the embryonal cell to produce an animal containing biofilament expressing and secreting cells; and (c) isolating the biofilament from the biofilament expressing and secreting cells from the animal.

In a sixth aspect, the invention features a method for producing a biofilament that includes the steps of: (a) providing an animal cell transfected with a nucleic acid molecule that contains (i) a nucleic acid sequence encoding a biofilament, (ii) a promoter that directs expression of a polypeptide in an animal cell, and (iii) a leader sequence that causes secretion of the biofilament by the cell; (b) culturing the transfected cell; and (c) isolating the biofilament from the culture medium of the cultured transfected cell. In other embodiments, the biofilament has a sequence that is 50% identical to SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, or SEQ ID NO: 32.

In one embodiment of the fifth and sixth aspects of the invention, the biofilament is spider silk (e.g., dragline silk). In another embodiment, the nucleic acid molecule contains an intron. In yet another embodiment, the animal is a mammal. In a preferred embodiment, when secreted such that the secretion is subjected to shear forces and mechanical extension, the biofilament has a poly-alanine segment that undergoes a helix to a β-sheet transition, where the transition forms a β-crystal that stabilizes the structure of the biofilament.

In another preferred embodiment of the fifth and sixth aspects of the invention, the biofilament has an amorphous domain that forms a β-pleated sheet such that inter-β sheet spacings are between 3 angstroms and 8 angstroms in size. In another preferred embodiment, the biofilament has a C-terminal amino acid motif containing an amorphous domain and a crystal forming domain, the motif having a sequence that is at least 50% identical to SEQ ID NO: 2. In yet another preferred embodiment, the biofilament has a consensus sequence that is at least 50% identical to SEQ ID NO: 3. In other embodiments, the biofilament has a sequence that is 50% identical to SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, or SEQ ID NO: 32.

In a preferred embodiment of all of the above aspects of the invention, where the biofilament is dragline silk, preferably the cell (or animal (e.g., a mammal) developed from the cell) produces both of the polypeptides (e.g., ADF-3 and ADF-4) required to produce the dragline silk at a ratio that is at least 40% of the ratio of these polypeptides produced in the natural source (e.g., in the spider).

By "biofilament" is meant a fibrous protein that is normally produced and secreted by any one of a variety of insects and arachnids. Biofilaments are composed of alternating crystalline and amorphous regions. Exemplary bio filaments include spider silk, an externally spun fibrous protein secretion found in a variety of arachnids (e.g., *Nephila clavipes*), and fibroin, an externally spun fibrous protein secretion found in a variety of insects (e.g., *Bombyx mori*). Preferable biofilaments, when secreted such that the secretion is subjected to shear forces and mechanical extension, have a poly-alanine segment, forming a crystal-forming domain, that undergoes a helix to β-sheet transition, forming a β-crystal that stabilizes its structure. Preferably, the amorphous domain of a biofilament forms a β-pleated sheet such that inter-β sheet spacings are between 3 angstroms and 8 angstroms in size, preferably, between 3.5 angstroms and 7.5 anstroms in size.

Preferably, a biofilament has a C-terminal portion with an amino acid repeat motif which is between 20 –40 amino acids in length, more preferably, 34 amino acids in length, and a consensus sequence which is between 35 and 55 amino acids in length, more preferably 47 amino acids in length. Preferably, a biofilament has an amino acid repeat motif (creating both the amorphous domain and the crystal-forming domain) having a sequence that is at least 50% identical to the sequence of SEQ ID NO: 2, more preferably, at least 70% identical, and most preferably, at least 90% identical to SEQ ID NO: 2. Preferably, a biofilament has a consensus sequence that is at least 50% identical to the sequence of SEQ ID NO: 3, more preferably, at least 70% identical, and most preferably, at least 90% identical to SEQ ID NO: 3.

By a "promoter" is meant a nucleic acid sequence sufficient to direct transcription. Also included in the invention are those promoter elements which are sufficient to render promoter-dependent gene expression controllable for cell type-specific, tissue-specific or inducible by external signals or agents; such elements may be located in the 5' or 3' regions of the native gene. Preferred promoters of the invention direct transcription of a protein in a milk-producing cell; such promoters include, without limitation, promoters from the following genes: whey acidic protein, αS1-casein, αS2-casein, β-casein, κ-casein, β-lactoglobin, and α-lactalbumin. Other preferred promoters of the invention direct transcription of a protein in a urine-producing cell (e.g., a uroepithelial cell or a kidney cell); such promoters include, without limitation, the promoter from the uroplakin gene. Yet another preferred promoter of the invention directs transcription of a protein in an embryonal cell.

By a "leader sequence" or a "signal sequence" is meant a nucleic acid sequence which, when operably linked to a nucleic acid molecule, allows for the secretion of the product of the nucleic acid molecule. The leader sequence is preferably located 5' to the nucleic acid molecule. Preferably, the leader sequence is obtain from same gene as the promoter that is used to direct the transcription of the nucleic acid molecule, or is obtained from the gene from which the nucleic acid molecule is derived.

By "culture medium" is meant the medium surrounding a cell, and in which the cell has been living. If the cell is secreting a protein (e.g., a biofilament), the culture medium of the cell will contain the protein secreted by that cell.

By a "transfected cell" or a "transformed cell" is meant a cell into which (or into an ancestor of which) has been introduced, by means of recombinant DNA techniques, a nucleic acid molecule encoding a polypeptide of the invention. Preferably, the cell is a eukaryotic cell from a multicellular animal (e.g., a mammal).

By an "embryonal cell" is meant a cell that is capable of being a progenitor to all the somatic and germ-line cells of an organism. Exemplary embryonal cells are embryonic stem cells (ES cells) and fertilized oocytes. Preferably, the embryonal cells of the invention are mammalian embryonal cells.

By "endogenous," as used herein in reference to a gene or a polypeptide, is meant a gene or polypeptide that is normally present in an animal.

By "germ-line cell" is meant a eukaryotic cell, progenitor, or progeny thereof, which is a product of a meiotic cell division.

By "operably linked" is meant that a nucleic acid molecule and one or more regulatory sequences (e.g., a promoter) are connected in such a way as to permit expression and/or secretion of the product (i.e., a polypeptide) of the nucleic acid molecule when the appropriate molecules (e.g., transcriptional activator proteins) are bound to the regulatory sequences.

By "transgene" is meant any piece of nucleic acid that is inserted by artifice into a cell, or an ancestor thereof, and becomes part of the genome of the animal which develops from that cell. Such a transgene may include a gene which is partly or entirely heterologous (i.e., foreign) to the transgenic animal, or may represent a gene homologous to an endogenous gene of the animal.

By "transgenic" is meant any cell which includes a nucleic acid sequence that has been inserted by artifice into a cell, or an ancestor thereof, and becomes part of the genome of the animal which develops from that cell. Preferably, the transgenic animals are transgenic mammals (e.g., rodents or ruminants). Preferably the nucleic acid (transgene) is inserted by artifice into the nuclear genome.

BRIEF DESCRIPTION OF THE DRAWING

FIG. 1A is a schematic representation of the goat β-casein/NcDS-1 construct containing the β-casein promoter and signal sequence, the 1.5 kb NcDS-1 cDNA, and the 3' UTR from β-casein.

FIG. 1B is a schematic representation of the Whey Acidic Protein (WAP)/NcDS-1 construct containing the WAP gene promoter, the WAP signal sequence, a 1.5 kb cDNA encoding dragline silk (NcDS-1), and the 3' end of the WAP gene.

FIG. 1C is a schematic representation of the uroplakin II/NcDS-1 construct containing the promoter and signal sequence from the uroplakin II gene, the NcDS-1 cDNA insert, and the 3' UTR region from the mouse protamine-1 (Mp-1) gene.

DETAILED DESCRIPTION

Biofilaments, such as spider silk, have a number of high performance mechanical properties that make them comparable to the "super-filaments" Spectra™ (commercially available from AlliedSignal) or Kevlar™ (commercially available from DuPont). Of particular importance is the energy to break a biofilament, which means that biofilaments can absorb energy when stretched, and dissipate that energy as heat when the stress is removed. Furthermore, biofilaments are resistant to digestion by proteolytic enzymes, and are insoluble in dilute acids and bases.

Biofilaments are a natural source of material that is renewable. Transgenic animals expressing biofilaments, such as the animals described herein, may be managed as normal livestock using available feedstuffs. Thus, the manufacture of this commodity is domestic and renewable. The truly natural source, the spiders themselves, are, unfortunately, too small to produce significant amounts of this material. In addition, since spiders manifest territorial behavior, they cannot be raised in close quarters for mass production.

The weight of the biofilament is important for ballistic protection applications. The demands in modem ballistic protection demand a flexible and light material that retains its unique mechanical properties. Biofilaments are lighter than Kevlar™, and are more flexible than Spectra™.

I. Spider Silk-encoding Genes

The size of the native dragline silk protein has not been determined conclusively, but has been observed to range from 274 kDa to 750 kDa. The N-terminus amino acid sequence and the 5'-end nucleic acid sequence have not been elucidated. Partial cDNA clones (spidroin 1 and 2) from *Nephilia clavipes* (the golden orb weaver found in Brazil and southern Florida) and from *Araneus diadematus* (Guerette et al., Science 272: 112–115, 1996) have been isolated and found to be part of the 3'-end of their corresponding genes. A summary of the clones isolated from Araneus, and the glands from which they are derived, is shown below in Table 1.

TABLE 1

*Araneus diadematus* genes
(libraries screened using spidroin-1, 2 from *N. clavipes*)
Distribution-Expression of specific silk type
(as determined by Northern Blot)

| Gene Cloned | major ampullae gland (producing dragline silk) | minor ampullae gland (producing accessory fiber) | flagelliform gland (producing viscid silk) | aggregate gland (producing viscid silk) | cyclindrical gland (producing cocoon silk) |
|---|---|---|---|---|---|
| ADF-1 | — | major | — | — | — |
| ADF-2 | — | — | — | — | minor |
| ADF-3 | major | — | minor | minor | — |
| ADF-4 | major | — | — | — | — |

The sequence of ADF-1 (*Araneus diadematus* fibroin) is 68% poly(A)$_5$ (i.e., AAAAA; SEQ ID NO: 9) or (GA)$_{2-7}$ (SEQ ID NOS: 10–15), and 32% GGYGQGY (SEQ ID NO: 16); ADF-2 is 19% poly(A)$_8$ (SEQ ID NO: 17) and 81% [GGAGQGGY (SEQ ID NO: 18) and GGQGGQGGYG-GLGSQGA (SEQ ID NO: 19)]; ADF-3 is 21% ASAAAAAA (SEQ ID NO: 20) and 79% [(GPGQQ)n, where n=1–8 (SEQ ID NO: 21–28) and GPGGQGPYGPG (SEQ ID NO: 29)]; and ADF-4 is 27% SSAAAAAAAA (SEQ ID NO: 30) and 73% [GPGSQGPS (SEQ ID NO: 31) and GPGGY (SEQ ID NO: 32)].

Any of a variety of procedures well known in the art may be utilized to clone additional biofilament-encoding genes using the known nucleic acid sequences from *Nephila* and *Araneus*, and one so skilled will routinely adapt one of these methods in order to obtain the desired gene. The full length clones of *Nephila* and *Araneus* genes may be likewise isolated.

One such method for obtaining a biofilament-encoding gene sequence is to use an oligonucleotide probe generated by the *Nephila clavipes* spidroin 1 gene sequence (Arcidiacono et al., Appl. Microbiol. Biotechnol. 49: 31–38, 1998) to screen an arachnid or insect cDNA or genomic DNA library for sequences which hybridize to the probe. Hybridization techniques are well known to the skilled artisan, and are described, for example, in Ausubel et al., supra, and Sambrook et al, supra. cDNA or genomic DNA library preparation is also well known in the art. A large number of prepared nucleic acid libraries from a variety of species are also commercially available. The oligonucleotide probes are readily designed using the sequences described herein and standard techniques. The oligonucleotide probes may be based upon the sequence of either strand of DNA encoding the spidroin 1 gene product. Exemplary oligonucleotide probes are degenerate probes (i.e., a mixture of all possible coding sequences for the *N. clavipes* spidroin 1 protein II. Spider Silk Formation and Spinning Silks or fibroin monomers are produced within specialized glands in the abdomen of the spider and are retained in a lumen at a concentration of 20–30%. This material will polymerize when tension is applied in the presence of drying. As the silk is very thin, the drying process is rapid. Silks are composed of alternating crystalline and amorphous regions. The dominant crystals are β-pleated sheet crystals that are arranged parallel to the long axis of the silk fiber. In *Bombyx morn* (silkworms), the crystal-forming domain is a six peptide (GAGAGS (SEQ ID NO: 1)) domain which alternates with amorphous domains.

The amino acids G, A, and S make up greater than 85% of silkworms' cocoon silk fibroin. Silk's alternating Ala or Ser and Gly residues extend to opposite sides of a given β-sheet so that the Ala side chains extending from one β-sheet efficiently nestle between those of the neighboring sheet, and likewise for the Gly side chains. Gly side chains from neighboring β-sheets are in contact, as are those of Ala and Ser. The inter-sheet spacings, consequently, have the alternating values 3.5 angstroms and 5.7 angstroms, as determined from X-ray diffraction studies of *Nephila* dragline silk. This spacing is identical to that of synthetic poly-L-alanine peptides in their β-sheet conformation. X-ray diffraction studies of *Araneuus diadematus* dragline silk indicates a larger inter-sheet spacing of about 7.5 angstroms (Gosline et al., Biomimetics: Design and Processing of Materials, pp:237–261, eds. Sarikaya and Aksay, Amer. Inst. of Physics, 1995).

In *Nephila*, the major ampullae gland (MA gland) produces the dragline silk. The C-terminal portion of the *Nephila* MA-gland produced genes cloned so far (spidroin 1 and spidroin 2) have the following sequences: a 34 amino acid long repeat motif (forming both the amorphous domain and crystal-forming domain); and a 47 amino acid long consensus sequence (Xu and Lewis, Proc. Natl. Acad. Sci. U.S.A. 87: 7120–7124, 1990; Beckwitt and Arcidiacono, J. Biol. Chem. 269: 6661–6663, 1994).

The 34 amino acid long repeat motif (forming both the amorphous domain and crystal-forming domain) of *Nephila* spidroin 1 has the following sequence: AGQ GGY GGL GSQ GAG RGG LGG QGA GAA AAA AAG G (SEQ ID NO: 2).

Note the poly-alanine region (AAAAAAA) at the C-terminal end of SEQ ID NO: 2, as well as numerous glycine blocks forming amorphous domains (two glycine residues separated by 3 amino acids; e.g., GG LGG).

The 47 amino acid long consensus sequence of *Nephila* spidroin 2 has the following sequence: CPG GYG PGQ QCP GGY GPG QQC PGG YGP GQQ GPS GPG SAA AAA AAA AA (SEQ ID NO: 3).

The silk is secreted within individual glands; when the secretion is subjected to shear forces and mechanical extension, the poly-alanine (crystal-forming) segments undergo a helix to β-sheet transition, forming β-crystals that stabilize its structure. The glycine blocks are designated as portions forming the amorphous polypeptide chains interspersed among the crystalline regions.

Biofilaments have evolved in certain insects and arachnids having very specialized anatomical adaptations and gene evolution. In spiders, the silk is produced by a series of abdominal glands. The formation and size of the crystal may depend upon, among other things, the primary amino acid sequence composition. The production and secretion of the major silks occurs in the major ampullae (MA) gland, the flagelliform (FL) gland, and the cylindrical (CY) gland, which produce dragline silk, viscid silk, and cocoon silk, respectively. It will be understood that the transgenic animals described herein, and the constructs used to generate such animals, may produce any of these biofilaments, or any variations thereof, such that a biofilament is produced having inter-β-sheet spacings of between 3.5 to 7.5 angstroms.

A. Dragline Silk

The MA gland produces two proteins, at a 3:2 ratio, which are rich in glycine, alanine, and proline. These proteins form the dragline silk, which is the lifeline, the scaffolding silk, and the frame for spider webs. Dragline silk is a high stiffness fiber and has properties similar to nylon. Dragline silk contains 20–30% crystal, by volume, and has the following characteristics: stiff (initial Young's modulus is 10 GPa), strong (tensile strength is 1.5 GPa), and tough (energy required to break is 150 $MJm^{-3}$).

B. Viscid Silk

The viscid silk produced by the FL gland forms the sticky spiral of the web. No genes encoding viscid silk have been identified as yet. Viscid silk contains less than 5% crystal by volume, is elastomeric in its native state, and has properties similar to Lycra. It has the following characteristics: mechanically similar to lightly cross-linked rubber (e.g., spandex), low stiffness (initial Young's modulus is 3 MPa), and highly extensible.

C. Cocoon Silk

The CY gland produces cocoon silk that is similar to the cocoon silk produced by silkworms (*B. mori*).

III. Synthesis of Biofilament Genes

Because of the difficulties encountered in cloning native silk genes, synthetic genes can be cloned and expressed. The cDNA sequences cloned to date share similarities in overall organization and in regions of sequence conservation. The consensus repeats are rich in glycine and glutamine, with poly (Ala) regions integrated into larger repeating units.

For discussion purposes, the candidate gene will be represented by one of the major dragline genes from *N. clavipes*, spidroin 1 (Arcidiacono et al., Appl. Microbiol. Biotechnol. 49: 31–38, 1998). The highly repetitive nature of these genes raises the concerns over the stability of the genes and the possibility of recombination. The repeats can be avoided based on suggestions offered, for example, by Arcidiacono et al., Appl. Microbiol. Biotechnol. 49: 31–38, 1998; Fahnestock and Irwin (supra). Furthermore, a series of constructs can be generated using a similar strategy (Fahnestock and Irwin, Appl. Microbiol. Biotechnol. 47: 23–32, 1997), generating 4–20 (or more) consecutive repeats, and can be tested in cell lines prior to the generation of transgenic animals. Blocks of synthetic repeats are constructed so they have different sizes and contain non-coding sequences (e.g., introns from casein or immunoglobulin genes) in order to facilitate transcription of the encoded biofilamenst and enhance expression. The blocks can be alternating using head-to-tail construct strategy (McGrath, K. P., Ph.D. Dissertation, University of Massachusetts at Amherst, 1991; Ferrari et al., U.S. Pat. No. 5,243,038).

Codon selection may also be designed to maximize expression, since premature termination may occur if the gene contains a greater number of codons recognized by tRNA species present in lower abundance in the cell (Rosenberg et al., J. Bacteriol. 175: 716–722, 1993, Manley, J. Mol. Biol. 125:407–432, 1978). The genes to be expressed are designed and synthesized using codons favored in the tissue being expressed (i.e.,casein genes in the mammary gland; uroplakins in the bladder).

Given the high frequency of alanine residues in biofilament proteins, it may be desirable to supplement the cell culture media of the the cell line with additional ala and/or gly amino acids to prevent the depletion of Ala tRNA and/or Gly tRNA pools from being the rate-limiting step to generating the biofilament protein.

IV. Assembly of Expression Vectors

Eukaryotic expression vectors may be generated which drive the synthesis and secretion of proteins (e.g., biofilament proteins) in the milk or urine of an animal transgenic for a nucleic acid molecule encoding such a protein. These vectors are prepared according to standard molecular biology techniques.

The synthesized nucleic acid molecule(s) may have a sequence encoding an epitope tag attached for easy identification and/or purification of the encoded polypeptide. Such purification may be accomplished, for example, by affinity chromatography for the epitope tag. A site-specific proteolytic or chemical agent recognition site may be added to the sequence to facilitate removal of the epitope tag following purification of epitope-tagged polypeptides (Saito et al., J. Biochem. 101: 123–134, 1987). Preferably, the sites and site-specific proteolytic agents cleave at or near the junction of the epitope tag and the biofilament protein.

A variety of chemical cleavage agents and their recognition sites (in single letter code) are known in the art, and include the following: Hydroxylamine (N or G); formic acid (D or P), cyanogen bromide (M); or acetic acid (D or P). For example, a cyanogen bromide (CNBr) may be used to cleave a Met (M) residue introduced between the epitope tag and the biofilament protein.

Alternatively, natural or synthetic proteases may be used. Examples of these (and their recognition sites) include enterokinase (DDDK; SEQ ID NO: 5); Factor Xa (IEGR; SEQ ID NO: 6); chymotrypsin (W and Y and F); renin (YIHPFHLL; SEQ ID NO: 7); trypsin (R and K); and thrombin (RGPR; SEQ ID NO: 8). For example, the epitope tag may be attached to the biofilament via a thrombin-recognition site. Following affinity purification of epitope tag-containing proteins, since biofilaments are generally resistant to proteolysis, the epitope tag may be easily removed upon proteolytic cleavage with thrombin.

The expression cassette consists of elements necessary for proper transcription, translation, and secretion in the desired eukaryotic cell (i.e., a promoter, signal sequence for secretion, intron sequences, and a polyadenylation signal). Many milk or urine specific promoters can be used with their signal sequences or with the silk and/or fibroin gene signal sequence. In the former case, the biofilament-encoding nucleic acid molecule should not contain its own translation initiation codon but, rather, should be in frame with the 3' end of the signal sequence. The 3' end of the biofilament-encoding nucleic acid molecule may contain its own polyadenylation signal, or may contain the 3' untranslated sequence normally found on the gene used for the promoter and/or signal sequence. For example, a biofilament-encoding nucleic acid molecule may be in an expression vector cassette with a promoter, signal sequence, and 3' untranslated sequence all from the same casein gene.

The eukaryotic expression constructs to be used may include one or more of the following basic components.

A) Promoter of Transcriptional Initiation Regulatory Region

These sequences may be heterologous to the cell to be modified and may include synthetic and natural viral sequences (e.g., human cytomegalovirus immediate early promoter (CMV); simian virus 40 early promoter (SV40); Rous sarcoma virus (RSV); or adenovirus major late promoter) which confers a strong level of transcription of the nucleic acid molecule to which they are operably linked. The promoter can also be modified by the deletion of nonimportant sequences and/or addition of sequences, such as enhancers (e.g., an enhancer element CMV, SV40, or RSV), or tandem repeats of such sequences. The addition of strong enhancer elements may increase transcription by 10–100 fold. Expression from the above-identified viral promoters is constitutive (i.e., expression occurs in the absence of an apparent external stimulus).

Alternatively, for expression in the milk, for example, the promoter region may be native to a ruminant mammary-specific gene. Examples include: αS1-casein (PCT Application Nos.: WO91/08216 and WO93/25567), αS2-casein, β-casein (Rosen, J. M., U.S. Pat. No. 5,304,489; Lee et al., Nucleic Acids Res. 16: 1027–1041, 1988), κ-casein, β-lactoglobin, and α-lactalbumin (Vilotte et al., Eur. J. Biochem. 186: 43–48, 1989; PCT Application No.: WO88/01648). These promoters can drive a high level of expression of a variety of proteins in a tissue and lactation specific manner.

B) Intron Inclusion

Genes containing an intron (i.e., genomic clones) are expressed at higher levels than intron-less genes. Hence, inclusion of an intron placed between the transcription initiation site and the translational start codon, 3' to the translational stop codon, or inside the coding region of the biofilament-encoding gene may result in a higher level of expression.

The intron sequence includes a 5' splice site (donor site) and a 3' splice site (acceptor site). Sequences of at least 100 base pairs are found between these two sites. The origin of these intronic sequences will be derived from the promoter being used, or from the native gene (Ichimura and Mita, J. Mol. Evol. 35: 123–130, 1992) and positioned 5' to the coding sequence of the silk or fibroin gene. Since the highly repetitive nature of the construct raises concerns over the stability of the gene and the possibility of recombination due to the repetitive sequences, they can be disrupted by inserting the introns of the gene from which the promoter is used. The introns can be positioned in a manner similar to those present in the fibroin gene of *Bombyx mori* (Tsujimoto and Suzuki, Cell 18: 591–600,1979; Tsujimoto and Suzuki, Cell 16: 425–436, 1979). This strategy will allow for increased levels of expression in addition to increased stability of the gene.

C) Signal (Leader) Sequences

Each expression vector will contain a signal sequence which directs the expressed gene product to be secreted from the mammary or uroepithelial cells. This signal sequence is present in any gene which is secreted naturally. A signal sequence from a relative fibroin gene (e.g., *B. mori* heavy and light fibroin gene, P25 and ssp160), from a gene specific to the tissue of expression (e.g., casein or uroplakin gene), or a general signal sequence (e.g., from human alkaline phosphatase, mellitin, and CD33 signal peptides) may be used. Furthermore, the signal sequences for secretion may be interchanged between mammalian/insect genes; for example, signal sequences from mellitin, casein, or the sequences from native silk (from arachnids) or fibroin (from insects) genes may be used.

D) Termination Region

The transcription termination region of the nucleic acid constructs may involve the 3'-end and polyadenylation signal from which the 5'-promoter region is derived. For example, the bovine αS1 casein gene. Alternatively, the 3'-end of the nucleic acid construct will contain transcription termination and polyadenylation signals which are known to regulate post-transcriptional mRNA stability such as those derived from bovine growth hormone, β-globin genes, or the SV40 early region.

E) Other Features of the Expression Vectors

The expression vectors designed for gene transfer also contain an origin or replication for propagation in *E. coli*, SV40 origin of replication, ampicillin resistance gene, neomycin resistance gene for selection in eukaryotic and/or genes (i.e., dihydrofolate reductase gene) that amplify the dominant selectable marker plus the gene of interest. In addition, the expression vectors may contain appropriate flanking sequences at their 5' and 3' ends that will allow for enhanced integration rates in the transduced cells (ITR sequences; Lebkowski et al., Mol. Cell. Biol. 8: 3988–3996, 1988). Furthermore, prolonged expression of the silk or fibroin protein in vitro may be achieved by the use of sequences (i.e., EBNA-1 and oriP from the Epstein-Barr virus) that allow for autonomous replication (the transduced, circular nucleic acid replicates as a plasmid in mammalian cells).

To clone and propagate large segments of DNA, cosmids are the vectors of choice. Although plasmid vectors can, in theory, carry large inserts, the resulting recombinants transform *Escherichia coli* very inefficiently. Cosmids have the capacity to propagate large pieces of foreign DNA (Royal et al., Nature 279: 125, 1979).

The expression vectors used for the generation of transgenic animals may be linearized by restriction endonuclease digestion prior to transformation of a cell. In a variant of this method, only a digestion fragment that includes the coding, 5'-end regulatory sequences (e.g., the promoter), and 3'-end regulatory sequences (e.g., the 3' untranslated region) from, for example, bovine casein or growth hormone sequences, will be used to transform cells. A cell transformed with such a fragment will not, consequently, contain any sequences that are necessary solely for plasmid propagation in bacteria (e.g., the cell will not contain the *E. coli* origin or replication or a nucleic acid molecule encoding an antibiotic-resistance protein (e.g., an ampicillin-resistance protein) that is useful for selecting prokaryotic cells).

In another variant of this method, the digestion fragment used to transform a cell will include the coding region, the 5' and 3' regulatory sequences, and a nucleic acid molecule (including a promoter and 3' untranslated region) encoding a protein capable of conferring resistance to a antibiotic useful for selecting eukaryotic cells (e.g., neomycin or puromycin).

The biofilament gene of interest may be modified in its 5' untranslated region (UTR), its 3' UTR, and/or its region coding for the N-terminus in order to preferentially improve expression. Alternatively, sequences within the coding sequence of the biofilament encoding-nucleic acid molecule may be deleted or mutated in order to increase secretion and/or avoid retention of the gene product within the cell due, for example, to the presence of endoplasmic reticulum (ER) retention signals or other sorting inhibitory signals. Furthermore, the transgenic construct may contain sequences that possess chromatin opening domain activity such that they confer reproducible activation of tissue-specific expression of a linked transgene (Ellis et al., PCT Application No.: WO95/33841; Chung and Felsenfield, PCT Application No.: WO96/04390).

V. Testing and Characterization of Expression Vectors

The assembled constructs are partially characterized by sequencing the areas where two pieces of DNA have been fused together by ligation. A partial restriction endonuclease map will provide information on the correct orientation of the ligated regulatory sequences with respect to the biofilament-encoding nucleic acid molecule.

Further characterization of the functionality of the assembled constructs include their transfection into established mammary epithelial cell lines (e.g., MAC-Ts) (see Turner and Huynh, U.S. Pat. No. 5,227,301; Huynh et al., Exp. Cell. Res. 197: 191–199, 1991; Stampfer et al., U.S. Pat. No. 4,423,145) and identification of the secreted product.

The recombinant DNA methods employed in practicing the present invention are standard procedures that are well known to those skilled in the art of molecular biology, and are described in detail in, for example, Sambrook, Fritsch and Maniatis, *Molecular Cloning: A Laboratory Manual* (2$^{nd}$ ed.), Cold Spring Harbor Press, 1989; Ausubel et al. *Current Protocols in Molecular Biology*, John Wiley & Sons, New York, N.Y., 1994; and Perbal, B. V., *A Practical Guide to Molecular Cloning* (2$^{nd}$ ed., John Wiley & Sons, New York, N.Y., 1988. For purposes of explanation only, the biofilament gene used in the following examples is the 1.5 kb NcDS-1 insert described and cloned by Arcidiacono et al., Appl. Microbiol. Biotechnol. 49: 31–38, 1998.

The following examples are meant to illustrate, and do not limit, the invention.

EXAMPLE 1

The Casein Promoter

In the following example, the design of the construct includes the use of the goat β-casein promoter (Ebert et al., Bio/Technology 12: 699–701, 1993), followed by its own signal sequence for expression, followed by a 1.5 kb insert containing the silk clone (Arcidiacono et al., supra) in frame with the 5' and 3' ends of the casein gene. A schematic diagram of this construct is shown in FIG. 1A.

The nucleic acid molecule encoding a biofilament (e.g., a silk or fibroin gene, or fragment thereof) is fused to the casein promoter and secretion of the biofilament protein is driven by signal sequences from the gene from which the promoter is derived, or from the biofilament nucleic acid molecule to be expressed. Termination sequences can be derived from the biofilament gene itself, or from the promoter gene. Furthermore, a hybrid gene can be created to increase the level of expression. For this purpose, the silk or fibroin gene (or fragment thereof) can be inserted between exon 2 (just upstream of the ATG) and exon 7 (downstream of the stop codon) of the goat β-casein gene (Ebert et al., Bio/Technology 12: 699–701, 1993). Since the highly repetitive nature of the construct raises concerns over the stability of the gene and the possibility of recombination due to the repetitive sequences, they can be disrupted by inserting the introns from the casein gene (introns 3 to 7). Construction of the vector can be performed in a cosmid vector (supercos), due to the large size of the final construct or the backbone of the plasmid could consist of any known bacterial vector (preferably ones that accept large DNA sizes) which contains sequences necessary for its amplification in an *E. coli* host (Sambrook et al., supra).

EXAMPLE 2

The Whey Acidic Protein (WAP) Construct

The present example demonstrates the generation of a hybrid gene composed of the WAP gene promoter, its signal sequence, a 1.5 kb cDNA encoding dragline silk (Arcidiacono et al, supra), followed by the 3' end of the WAP gene (Velander et al., Proc. Natl. Acad. Sci U.S.A. 89: 12003–12007, 1992). The details of its construction are described below and diagrammed in FIG. 1B.

Whey acidic protein (WAP), the major whey protein in rodents, is expressed at high levels exclusively in the mammary gland during late pregnancy and lactation (Hobbs et al., J. Biol. Chem. 257: 3598–3605, 1982). The genomic murine WAP gene consists of 2.6 kbp (kilo base pairs) of 5' flanking promoter sequence, 3.0 kbp of coding sequence (exons and introns), and 16 kbp of 3' flanking DNA (see FIG. 1B) (Velander et al., Proc. Natl. Acad. Sci U.S.A. 89: 12003–12007, 1992; Velander et al., Ann. N.Y. Acad Sci. 665: 391–403, 1992).

In one example, a hybrid gene composed of the WAP gene promoter and a cDNA encoding dragline silk may be constructed. The hybrid dragline-silk encoding gene is created by inserting the gene(s) or nucleic acid molecule(s) of interest (in this case, a cDNA encoding dragline silk) between the murine WAP promoter and 5' sequence (nucleotide position −949 to +33) at the 5' end and the WAP 3' sequence at the 3'∝end (843 bp; portion of exon 3, last 30 bases and all of intron C, exon 4, and 70 bp of 3' UTR) (Campbell et al., Nucleic Acids Res. 12: 8685–8697, 1984). In this example, the signal sequence comes from the native silk gene. One can also use the WAP gene signal sequence by including an additional 56 bp at the 5' end (position −949 to +89).

In another example, the hybrid gene is created by inserting nucleotide sequence encoding part of the 5' untranslated region and a 19 amino acid signal sequence from the murine WAP gene (nucleotides +1 to +90) (Hennighausen et al., Nucl. Acids Res. 10: 3733–3744, 1982), and by amplifying the 1.5 kb (kilo base) silk gene (NsDS-1; Arcidiacono et al., supra) using 5' primers containing the 90 bp (base pair) sequence encoding the signal sequence flanked by a KpnI restriction endonuclease recognition site. The amplification is performed to maintain the correct reading frame, and 3' primers creating a KpnI restriction endonuclease recognition site at the 3' end of the gene. This PCR product is then insert at the KpnI site at the first exon of WAP. The hybrid gene can be cut out of the vector by digestion with the EcoRI restriction endonuclease (see FIG. 1B), and purified for microinjection.

EXAMPLE 3

The Uroplakin Promoter

In these experiments, the uroplakin II promoter (Lin et al., Proc. Natl. Acad. Sci. U.S.A. 92:679–683, 1995; Sun, T., PCT Application No.: WO96/39494) is used to drive the expression of the fibroin or silk gene(s) in the urothelium of transgenic animals. The fibroin or silk gene(s) is inserted downstream of a 3.6 kb 5' flanking sequence of the mouse uroplakin II (UPII) gene (Lin et al., Proc. Natl. Acad. Sci. U.S.A. 92:679–683, 1995). A sequence containing part of exon 1 and all of intron 1 and exon 2 of the mouse protamine-1 (Mp-1) gene (Peschon et al., Proc. Natl. Acad. Sci. U.S.A. 84: 5416, 1987) is placed at the 3' end of the gene to provide an exon/intron splicing site and a polyadenylation signal. One can also use the signal sequence of the uroplakin II gene by inserting the fibroin or silk-encoding gene, or fragment thereof (mature protein only), in frame to amino acid 59 of exon 3. A diagram of this construct is shown on FIG. 1C.

EXAMPLE 4

DNA Shuffling

Another method for producing a biofilament-encoding gene cassette is by DNA shuffling. DNA shuffling is a process for recombination and mutation, performed by random fragmentation of a pool of related genes, followed by reassembly of the fragments by primerless PCR (Stemmer, W. P., Nature 370: 389–391, 1994; Stemmer, W. P., Proc. Natl. Acad. Sci. U.S.A. 91: 10747–10751, 1994). The goal of DNA shuffling is to optimize the function of genes without first determining which gene product is rate limiting. Genes themselves can be "shuffled," or can be from different species (i.e., spidroin 1 and 2 and ADF 1–4). Furthermore, different repeats (e.g., GGAGQGGY (SEQ ID NO:4) from ADF 3) within one species can be "shuffled" (with, for example, repeats from ADF 1, 2, and 4) and expressed to determine the combination which yields favorable characteristics. In addition to point mutation, diversity is generated using a wide variety of mutational mechanisms, such as polynucleotide deletion, insertion, and inversion, as well as integration and excision. Once thus generated, the biofilament-encoding nucleic acid molecule may be inserted into an expression cassette for secretion in milk or urine, and used to transform mammalian cells.

EXAMPLE 5

Constructs Expressing Two Genes

For the expression of two genes (e.g., dragline silk consists of a ratio of ADF3 and 4), either two separate constructs can be generated, or both genes can be cloned into the same expression cassette with the insertion of an intervening ribosomal entry site (IRES) (Jang et al., J. Virol. 62: 2636–2643, 1988). The advantage to cloning both genes into the same expression cassette is that only one single construct is needed to generate the transgenic animal.

EXAMPLE 6

Synthesis of Chimeric or Hybrid Biofilaments

Chimeric molecules are synthesized that include a fusion of the silk (containing either crystal or amorphous domains) in frame with one or more domains of collagen or fibrillin, that may allow for increased crosslinking, stability, or elasticity. Such a chimera is especially useful as a surgical biomaterial.

EXAMPLE 7

Production of Biofilaments in Mammary Epithelial or Uroepithelial Cell Lines

The synthesized biofilament-encoding nucleic acid molecules of the invention are produced in homologous biologically relevant cell culture systems. Genetic stability of the synthetic genes, secretion ability, and attributes of the produced biofilament(s) can, thus, be evaluated very efficiently before transgenic animal studies are initiated.

Mammary epithelial and urine-producing cell lines are transfected according to standard techniques (see, e.g., Ausubel et al., supra) with their respective plasmids (e.g., a milk-specific promoter containing expression construct is transfected into mammary epithelial cells). In one example, to demonstrate the secretion of the produced spider silk(s), culture media is harvested from the stable cell lines (24–96 hours post-differentiation for mammary epithelial cells) and resolved by SDS-PAGE for Western blotting analysis using anti-spider silk antibodies (commercially available from Monsanto, St. Louis, Mo.), or antibodies raised against peptides having sequences homologous to SEQ ID Nos: 1–4.

EXAMPLE 8

Generation of Transgenic Animals Expressing Biofilament(s) in Milk or Urine

In some methods of trangenesis, transgenes are introduced into the pronuclei of fertilized oocytes. For some animals, such as mice, fertilization is performed in vivo and fertilized ova are surgically removed. In other animals, the ova can be removed from live, or from newly-dead (e.g., slaughterhouse) animals and fertilized in vitro. Transgenes are usually introduced by microinjection (Ogata et al., U.S. Pat. No. 4,873,292). The microinjected zygotes are transferrred to an appropriate female resulting in the birth of a transgenic or chimeric animal, depending upon the stage of development when the transgene is integrated. Chimeric animals can be bred to form true germline transgenic animals.

Alternatively, transgenes can be introduced into embryonic stem cells (ES cells). Transgenes can be introduced into such cells by electroporations, microinjection, or any other techniques used for the transfection of cells which are known to the skilled artisan. Transformed cells are combined with blastocysts from the animal from which they originate. The cells colonize the embryo, and in some embryos these cells form the germline of the resulting chimeric animal (Jaenisch, R., Science 240: 1468–1474, 1988). Alternatively, ES cells can be used as a source of nucleic for transplantation into an enucleated fertilized oocytes, thus giving rise to a transgenic animal.

Production of a Biofilament in Milk

In one example, the spider silk gene is subcloned into an expression vector that contains a casein gene promoter, such that the expression of the spider silk gene is controlled by the casein gene promoter. One such expression vector is a casein expression vector based on the vectors described by Rosen, J. M. (U.S. Pat. No. 5,304,489) and Meade and Lonberg (U.S. Pat. No. 4,873,316).

In another example, the WAP/silk gene hybrid fragment (the EcoRI fragment described above in Example 2) is purified and microinjected into fertilized mouse eggs, which are then implanted into foster mothers. The presence of the WAP/silk gene is identified by Southern blot analysis of tail DNA (DNA isolated from tail tissue) in accordance with methods well known in the art. Positive founder animals are then back-crossed to generate hemizygous animals that are used for studying transgene expression.

Production of a Biofilament in Urine

The spider silk gene, for example, may be subcloned into an expression vector such that the spider silk gene is under the transcriptional control of the uroplakin promoter (described by Lin et al., Proc. Natl. Acad. Sci. U.S.A. 92:679–683, 1995).

Urine has the added advantage that its pH and salt composition can be modulated to allow for the incorporation of certain components that may influence the formation of the silk in a most native structure.

EXAMPLE 9

Generation of "Double Transgenic" Animals that Produce Biofilaments in Both Milk and Urine A transgenic animal may be generated that produces a biofilament protein (e.g., spider silk) in both its urine and its milk. One method for constructing such an animal is to transform an embryonal cell of the animal with two constructs, one construct in which the expression of the biofilament-encoding nucleic acid molecule is directed by a promoter capable of expressing and secreting the biofilament from a milk-producing cell; and a second construct in which the expression of the biofilament-encoding nucleic acid molecule is directed by a promoter capable of expressing and secreting the biofilament from a urine-producing cell. In this method, the doubly-transformed cell is used to generate a transgenic animal.

Hence, mammalian (e.g., ruminant) zygotes are microinjected (or co-microinjected) with two nucleic acid fragments: one that expresses the biofilament protein under the control of a milk promoter, and one that expresses the biofilament protein under the influence of a urine specific promoter. The generated transgenic animal will be secreting/producing the biofilament in both its milk and in its urine. This will increase the total output of biofilaments produced per transgenic animal unit.

A second method for producing such an animal capable of producing a biofilament in both its milk and its urine is to separately generate an embryonic stem cell carrying a construct capable of expressing and secreting the biofilament in a milk-producing cell and an embryonic stem cell carrying a construct capable of expressing and secreting the biofilament in a urine-producing cell. Both transformed ES cell types are then combined with blastocysts from the animal from which they originate to produce chimeric animals, which may then be bred to homozygosity.

This type of double-expressing animal has a number of advantages. First, animals of both genders will produce biofilaments in the urine on a continual basis from birth, and female animals will then be able to produce additional biofilament protein in their milk as a lactating adult. And second, the amount of biofilament produced by any individual female animal may be increased (by inducing lactation) or reduced (by not inducing lactation) as the need for biofilament changes.

EXAMPLE 10

Generation of Transgenic Animals That Coexpress and Assemble a Biofilament Protein from two Monomers A transgenic animal may be generated that produces two proteins which are both required for the correct assembly of a biofilament protein in its milk, urine, or both. For example, *Araneus diadematus* dragline silk consists of a ratio of ADF3 and 4). One method for constructing such an animal is to transform an embryonal cell of the animal with two constructs, each expressing one the two proteins. These proteins may be expressed in the urine or milk, or both.

In a second method, the construct described in Example 5 which encodes a polycistronic message may be employed. This construct may be able to secrete its products in the milk, urine, or both. Once the two proteins are present in the same fluid (i.e., both in the milk or both in the urine), they can assemble correctly and be purified.

---

What is claimed is:

1. A transgenic female ruminant comprising germline and somatic cells that comprise a nucleic acid molecule comprising a mouse whey acidic protein (WAP) promoter operably linked to a nucleotide seciuence encoding a polypeptide, wherein the polypeptide comprises a biofilament polypeptide and a leader sequence that enables secretion of the biofilament polypeptide by milk-producing cells into milk of the ruminant, wherein the biofilament polypeptide is a dragline silk polypeptide selected from the group consisting of *Araneus diadematus* fibroin-3 ("ADF-3"), *Araneus diadematus* fibroin-4 ("ADF-4"), *Neyhila clavipes* dragline silk-1 ("NcDS-1"), and *Nephila clavipes* dragline silk-2 ("NcDS-2"), and wherein the ruminant secretes the biofilament polypeptide into milk.

2. A method for producing a biofilament polypeptide, comprising: providing a transgenic female ruminant of claim 1 and isolating the biofilament polypeptide from milk produced by the transgenic female ruminant.

3. The transgenic female ruminant of claim 1, wherein the biofilament polypeptide is ADF-3.

4. The transgenic female ruminant of claim 1, wherein the biofilament polypeptide is ADF-4.

5. The transgenic female ruminant of claim 1, wherein the biofilament polypeptide is NcDS-1.

6. The transgenic female ruminant of claim 1, wherein the biofilament polypeptide is NcDS-2.

* * * * *